United States Patent [19]

Sato et al.

[11] Patent Number: 5,180,586

[45] Date of Patent: Jan. 19, 1993

[54] ACARICIDAL COMPOSITION

[75] Inventors: Toshiya Sato; Hamako Hata, both of Tokyo, Japan

[73] Assignee: Takasago International Corporation, Tokyo, Japan

[21] Appl. No.: 599,575

[22] Filed: Oct. 18, 1990

[30] Foreign Application Priority Data

Oct. 19, 1989 [JP] Japan ................. 1-272401

[51] Int. Cl.$^5$ ............................. A01N 25/00
[52] U.S. Cl. ................... 424/405; 424/406; 424/407; 424/408; 424/409
[58] Field of Search ........... 424/405, 406, 408, 409, 424/76.8, 45, 46; 514/520, 526

[56] References Cited

U.S. PATENT DOCUMENTS

| | | | |
|---|---|---|---|
| 3,259,648 | 7/1968 | Hennis | 424/343 |
| 4,045,551 | 8/1977 | Ueno et al. | 424/76 |
| 4,368,207 | 1/1983 | Lover et al. | 424/343 |
| 4,666,940 | 5/1987 | Bischoff et al. | 514/544 |
| 4,800,196 | 1/1989 | Nomura et al. | 514/159 |
| 4,931,469 | 6/1990 | Black et al. | 514/617 |

FOREIGN PATENT DOCUMENTS

| | | |
|---|---|---|
| 0235722 | 2/1987 | European Pat. Off. . |
| 674743 | 1/1930 | France . |
| 2392602 | 12/1978 | France . |
| 61-57501 | 3/1986 | Japan . |
| 62-33106 | 2/1987 | Japan . |
| WO8912673 | 12/1989 | PCT Int'l Appl. . |
| WO9009738 | 9/1990 | PCT Int'l Appl. . |
| 1368657 | 10/1974 | United Kingdom . |

OTHER PUBLICATIONS

Chemical Abstracts, vol. 88, No. 3, Jan. 16, 1978, p. 163, Abstract No. 17260z, Columbus, Ohio, US, R. S. Desphande et al.: "Insecticidal Activity of Ocimum Basilicum Linn", & Pesticides 1977, 11(5), 11–12.

Chemical Abstracts, vol. 90, No. 19, abstract No. 147035g.

Derwent Abstracts May 12, 1982, abstract No. 21087 E/11.

The Merck Index (1983) p. 1078.

Shoyakugaku Zasshi, 43(2), pp. 163–168 (1989).

*Primary Examiner*—Thurman K. Page
*Assistant Examiner*—Robert Harrison
*Attorney, Agent, or Firm*—Sughrue, Mion, Zinn, Macpeak & Seas

[57] ABSTRACT

An acaricidal composition is disclosed, comprising one or more compounds selected from among methyl cinnamate, ethyl cinnamate, n-propyl cinnamate, isopropyl cinnamate, n-butyl cinnamate, isobutyl cinnamate, isoamyl cinnamate, n-hexyl cinnamate, allyl cinnamate, cinnamyl acetate, cinnamyl propionate, cinnamyl n-butyrate, cinnamyl isobutyrate, p-cresyl acetate, p-cresyl butyrate, p-cresyl isobutyrate, p-methylbenzyl propionate, β-phenoxyethyl alcohol, phenoxyethyl acetate, phenoxyethyl propionate, phenoxyethyl n-butyrate, phenoxyethyl isobutyrate, methyl phenylacetate, ethyl phenylacetate, dibenzyl ether, heliotropin, methyl diphenyl ether and 2-methyl-1-methylbicyclo[2.2.1]hept-5-en-2-yl)-1-penten-3-ol as an active ingredient.

5 Claims, No Drawings

ACARICIDAL COMPOSITION

FIELD OF THE INVENTION

This invention relates to an acaricidal composition. More particularly, it relates to an acaricidal composition which is highly safe to the human body and exerts an excellent effect of exterminating house dust acari.

BACKGROUND OF THE INVENTION

House dust acari inhabit and propagate mainly in highly moist places, for example, on the surface of the floor, under or within the floor spreads such as tatami or carpet or within bedclothes. Recently, Dermatophagoides including *Dermatophagoides pteronyssinus* and *Dermatophagoides farinae*, which amount to 90% of these house dust acari, have become a serious problem since they are important allergens causing bronchial asthma, allergic rhinitis and atopic dermatitis.

The most effective method for exterminating these acari is to well ventilate and dry a house. However, the recent increase in houses of a closed structure and changes in life style make it more and more difficult to sufficiently ventilate a room. Under these circumstances, the damage by acari has become more and more serious.

In order to exterminate these acari, various acaricides (for example, organophosphorus compounds such as fenitrothion, fenthion, dichlorvos, diazinon; carbamate compounds such as propoxur, carbaryl; pyrethroid compounds such as resmethrin, phenothrin, permethrin) have been applied in the form of an aerosol, fumigant, insecticidal sheet or impregnating agent for, for example, carpet. Furthermore, it is recently proposed to use compounds other than those cited above for exterminating acari. For example, JP-A-61-57501 discloses to use a combination of acaricidal compounds such as benzyl benzoate, benzyl salicylate or dibutyl phthalate with a powdery cleanser and describes that the acaricidal effect of benzyl benzoate has been physiologically studied well in particular. (The term "JP-A" as used herein means an "unexamined published Japanese patent application".) JP-A-61-91103 discloses an acaricide which comprises benzyl benzoate and an aliphatic hydrocarbon as the major components. Further, JP-A-61-87603 discloses benzyl salicylate and phenethyl benzoate while JP-A-62-33106 discloses phenyl salicylate, phenyl benzoate, diphenylamine, methyl β-naphthyl ketone and coumarin each as an active ingredient for an acaricide. Furthermore, JP-A-64-19004 discloses an acaricide comprising benzaldehyde or perillaldehyde, l-carvone or d-carvone, methyl salicylate or ethyl salicylate, or methyl benzoate or ethyl benzoate as an active ingredient. Regarding natural substances, furthermore, JP-A-63-104905 discloses that terpene compounds are available as a preventing agent of acari. Furthermore, it is known that other vegetables essential oils (for example, bitter almond oil, wintergreen oil) show an acaricidal effect (F. Watanabe et al., *Shoyakugaku Zasshi*, 43 [2], 163–168 (1989)).

However, typical known acaricidal compounds (namely, organophosphorus compounds and carbamate compounds) generally show a high toxicity and exert undesirable effects on the human body. Therefore, it is undesirable to use these compounds indoors or around houses. These compounds are further disadvantageous in that their effects on Dermatophagoides causing allergic diseases are limited. On the other hand, pyrethroid compounds are expensive and show only limited effects on house dust acari, though they are less toxic in general. Other acaricidal compounds are also disadvantageous in the limited effects on Dermatophagoides.

Accordingly, it has been urgently required to develop an acaricide which is highly safe to the human body, can be easily used anywhere in a house and yet exerts an intense effect of exterminating a number of house dust acari including Dermatophagoides causing allergic diseases.

SUMMARY OF THE INVENTION

Under these circumstances, the present inventors have conducted extensive studies in order to provide an acaricide which is highly safe to the human body and widely exerts an excellent extermination effect on house dust acari. As a result, they have found that the following compounds which have been used as a perfume in foods and cosmetics for a long time and thus proved to be safe to the human body are highly effective in the extermination of house dust acari, thus completing the present invention.

Accordingly, the present invention provides an acaricidal composition comprising one or more compounds selected from among methyl cinnamate, ethyl cinnamate, n-propyl cinnamate, isopropyl cinnamate, n-butyl cinnamate, isobutyl cinnamate, isoamyl cinnamate, n-hexyl cinnamate, allyl cinnamate, cinnamyl acetate, cinnamyl propionate, cinnamyl n-butyrate, cinnamyl isobutyrate, p-cresyl acetate, p-cresyl butyrate, p-cresyl isobutyrate, p-methylbenzyl propionate, β-phenoxyethyl alcohol, phenoxyethyl acetate, phenoxyethyl propionate, phenoxyethyl n-butyrate, phenoxyethyl isobutyrate, methyl phenylacetate, ethyl phenylacetate, dibenzyl ether, heliotropin, methyl diphenyl ether and 2-methyl-1-(methylbicyclo[2.2.1]hept-5-en-2-yl)-1-penten-3-ol as an active ingredient.

DETAILED DESCRIPTION OF THE INVENTION

The acari to be exterminated with the acaricidal composition of the present invention include not only house dust acari inhabiting and propagating indoors, for example, Pyroglyphidae such as *Dermatophagoides farinae* and *Dermatophagoides pteronyssinus*; Acaridae such as *Typophaqus putrescentiae* and *Aleuroglyphus ovatus*; Glycyphagidae such as *Glycyphagus privatus* and *Glycyphagus domesticus*; and Cheyletidae such as *Cheyletus malaccensis* and *Cheyletus fortis*; but animal-parasitic acari, for example, Marcronyssidae such as *Ornithonyssus bacoti* and *Ornithonyssus sylviarum*.

The acaricidal composition of the present invention may contain one of the above-mentioned active ingredients or a combination thereof as such. In general, however, it may be formulated into an oil preparation, emulsifiable concentrate, wettable powder, spray, aerosol, fumigant, coating, detergent, dust, granule or capsule by supporting on a solid or liquid carrier and optionally adding various additives, for example, a film-forming agent, emulsifier, sticking agent, dispersant, wetting agent, stabilizer, propellant or volatility-controller, if required.

Examples of the solid carrier to be used herein include mineral powders such as silicic acid, kaolin, activated carbon, bentonite, diatomaceous earth, talc and calcium carbonate; vegetable powders such as wheat flour and starch; and synthetic polymer powders such as polyvinyl chloride powder. Examples of the liquid carrier include water; aliphatic hydrocarbons such as hexane, kerosene and coal oil; aromatic hydrocarbons such as benzene, toluene and xylene; halogenated hydrocarbons such as dichloroethane and carbon tetrachloride; alcohols such as ethanol, isopropyl alcohol and ethylene glycol; ketones such as acetone, methyl ethyl ketone and cyclohexanone; ethers such as tetrahydrofuran, dimethoxyethane and diethyl ether; esters such as ethyl acetate; nitriles such as acetonitrile; acid amides such as dimethylformamide; and vegetable oils such as soybean oil and cottonseed oil.

Examples of the film-forming agent include cellulose derivatives, vinyl resins, alkyd resins, urea resins, epoxy resins, polyester resins, urethane resins, silicone resins, acrylic resins, chlorinated rubbers and polyvinyl alcohol. Examples of the emulsifier, sticking agent and dispersant include surfactants such as soaps, polyoxyethylene alkylaryl ethers, polyoxyethylene fatty acid esters, fatty acid glycerols, sorbitan fatty acid esters, higher alcohol sulfates and alkylarylsulfonic acid salts. Examples of the propellant include liquefied petroleum gas, Freon gas and dimethyl ether. Examples of the volatility-controller include tricyclodecane and cyclododecane.

Furthermore, the active ingredient(s) may be used together with sublimating insecticides such as paradichlorobenzene, naphthalene or camphor so as to give a sublimating solid preparation.

Moreover, the acaricidal composition of the present invention may contain, for example, various conventional insecticides, acaricides, synergists, harmful insect repellents, rodent repellents, bactericides, fungicides, perfumes or colorants used for exterminating harmful insects, such as fenitrothion, propoxur or resmethrin.

The content of the above-mentioned active ingredient in the acaricidal composition of the present invention may vary depending on the formulation, application means and the place to be applied. It is generally preferable that the total content of the active ingredient(s) ranges from 0.1 to 50% by weight (in the case of a wettable powder or emulsifiable concentrate) and from 0.1 to 30% by weight (in the case of an oil preparation or aerosol), respectively.

The acaricidal composition of the present invention thus prepared may be used in, for example, a floor, tatami, a carpet, bedclothes, a sofa, a pillow or a closet by applying, spraying, coating, transpiring or placing. Alternatively, it may be used as a detergent for human or pet animals. The dose may be preferably approximately 80 mg or more per $m^2$ of the area to be treated or approximately 8 mg or above per $m^3$ of the space to be treated, in terms of the total amount of the active ingredient(s).

In addition to the above formulations, the acaricide of the present invention may be formulated into a film, sheet or constructional material having an acaricidal activity by supporting the active ingredient(s) on an appropriate substrate. Examples of the substrate to be used herein include sheets of synthetic resins such as polyethylene, polypropylene, nylon, polyvinyl chloride or polyesters; animal or vegetable fibrous materials or inorganic fibrous materials such as paper, cloth, non-woven cloth and leather; mixed sheets of the above-mentioned synthetic resins and animal, vegetable or inorganic fibers; mixed fabrics or non-woven fabrics; foils or films of metals such as aluminum, stainless steel or zinc; laminates of the above-mentioned sheets; and various natural wooden materials and plastic molded articles employed for construction purposes. The active ingredient of the acaricidal composition of the present invention is supported on these substrates by coating, impregnating, dropping or cofabricating to give an acaricidal material. The amount of the active ingredient in the substrate is not particularly restricted but may be optionally selected. In the case of impregnation, it is preferable to use the active ingredient in the saturation amount.

The acaricidal material thus obtained may be preferably used, for example, in the following manner. A polymer sheet (for example, polypropylene) impregnated with the active ingredient of the present invention is placed under tatami, a carpet or sofa. In this case, it is preferable to use the active ingredient at a ratio of from approximately 0.5 to 20 g per unit area. The impregnation of the polymer with the active ingredient makes the sustained release of the active ingredient possible, which brings about a sustained acaricidal effect.

The effects of the active ingredients of the present invention are examined by using *Dermatophagoides pteronyssinus* which is one of Dermatophagoides and is generally less sensitive to chemicals.

Namely, a filter paper (5 mm × 5 mm) is impregnated with each test compound in such a manner as to give a definite concentration. A liquid compound is used as such while a solid one is dissolved in acetone. In accordance with a method reported by Watanabe et al., *Shoyakugaku Zasshi*, 43 [2], 163–168 (1989), the filter sheet is introduced into a cylindrical container (approximately 20 cc) containing 50 to 80 head of *Dermatophagoides pteronyssinus* together with a bait. The container is then sealed with a Teflon stopper and allowed to stand in an incubator at 25° C. After 24 hours and 48 hours, the life or death of the acari is examined under a stereoscopic microscope or a loupe (×25) and evaluated. The procedure is repeated thrice and the lethality is calculated according to the following equation. Table 1 shows average values.

$$Lethality\ (\%) = (X - Y)/X \times 100$$

X: number of living acari in untreated plot; and
Y: number of living acari in treated plot.

In Table 1, a mixture of test compounds is expressed in the compound number of each component.

For comparison, permethrin and benzyl salicylate, which are conventional acaricides, are also evaluated in the same manner. The results are shown in Table 1.

TABLE 1

| Type | Compound No. | Test Compound (blending ratio) | Lethality | | | |
|---|---|---|---|---|---|---|
| | | | Dose of active ingredient (0.08 g/$m^2$) | | Dose of active ingredient (0.04 g/$m^2$) | |
| | | | After 24 hours | After 48 hours | After 24 hours | After 48 hours |
| Single compound | (1) | Methyl cinnamate | 100 | 100 | 100 | 100 |
| | (2) | Ethyl cinnamate | 100 | 100 | 100 | 100 |

TABLE 1-continued

| Type | Compound No. | Test Compound (blending ratio) | Lethality | | | |
|---|---|---|---|---|---|---|
| | | | Dose of active ingredient (0.08 g/m$^2$) | | Dose of active ingredient (0.04 g/m$^2$) | |
| | | | After 24 hours | After 48 hours | After 24 hours | After 48 hours |
| | (3) | n-Propyl cinnamate | 86 | 100 | 78 | 90 |
| | (4) | Isopropyl cinnamate | 92 | 100 | 82 | 98 |
| | (5) | n-Butyl cinnamate | 80 | 100 | 75 | 90 |
| | (6) | Isobutyl cinnamate | 82 | 100 | 71 | 75 |
| | (7) | Isoamyl cinnamate | 88 | 100 | 76 | 100 |
| | (8) | n-Hexyl cinnamate | 82 | 100 | 58 | 62 |
| | (9) | Allyl cinnamate | 79 | 100 | 72 | 100 |
| | (10) | Cinnamyl acetate | 100 | 100 | 53 | 82 |
| | (11) | Cinnamyl propionate | 100 | 100 | 65 | 89 |
| | (12) | Cinnamyl n-butyrate | 80 | 100 | 53 | 72 |
| | (13) | Cinnamyl isobutyrate | 100 | 100 | 62 | 85 |
| | (14) | p-Cresyl acetate | 85 | 100 | 80 | 98 |
| Single compound | (15) | p-Cresyl butyrate | 92 | 100 | 83 | 97 |
| | (16) | p-Cresyl isobutyrate | 90 | 100 | 78 | 85 |
| | (17) | p-Methylbenzyl propionate | 95 | 100 | 86 | 96 |
| | (18) | β-Phenoxyethyl alcohol | 100 | 100 | 96 | 100 |
| | (19) | Phenoxyethyl acetate | 100 | 100 | 86 | 98 |
| | (20) | Phenoxyethyl propionate | 100 | 100 | 78 | 85 |
| | (21) | Phenoxyethyl n-butyrate | 100 | 100 | 82 | 98 |
| | (22) | Phenoxyethyl isobutyrate | 100 | 100 | 100 | 100 |
| | (23) | Methyl phenylacetate | 100 | 100 | 100 | 100 |
| | (24) | Ethyl phenylacetate | 100 | 100 | 100 | 100 |
| | (25) | Dibenzyl ether | 100 | 100 | 100 | 100 |
| | (26) | Heliotropin | 100 | 100 | 100 | 100 |
| | (27) | Methyl diphenyl ether | 100 | 100 | 100 | 100 |
| Single compound | (28) | 2-Methyl-1-(methylbicyclo[2.2.1]hept-5-en-2-yl)-1-penten-3-ol | 100 | 100 | 69 | 100 |
| Mixed Composition | | (2)/(15) (1/1) | 100 | 100 | 100 | 100 |
| | | (2)/(18) (1/1) | 100 | 100 | 100 | 100 |
| | | (2)/(24) (1/1) | 100 | 100 | 100 | 100 |
| | | (2)/(27) (1/1) | 100 | 100 | 100 | 100 |
| | | (14)/(18) (1/1) | 100 | 100 | 98 | 100 |
| | | (14)/(23) (1/1) | 100 | 100 | 90 | 100 |
| | | (14)/(25) (1/1) | 100 | 100 | 100 | 100 |
| | | (14)/(27) (1/1) | 100 | 100 | 100 | 100 |
| | | (2)/(18)/(24) (1/1/1) | 100 | 100 | 92 | 100 |
| | | (24)/(25)/(27) (1/1/1) | 100 | 100 | 100 | 100 |
| | | (25)/(26)/(27) (1/1/1) | 100 | 100 | 90 | 100 |
| Comparison | | Permethrin | 82 | 90 | 63 | 83 |
| | | Benzyl salicylate | 50 | 70 | 25 | 32 |

As Table 1 clearly shows, the active ingredients of the acaricide of the present invention were superior to permethrin and benzyl salicylate in the effect of exterminating *Dermatophagoides pteronyssinus*.

To further illustrate the present invention, and not by way of limitation, the following Examples will be given.

EXAMPLE 1

| Oil Preparation: | |
|---|---|
| | (parts by weight) |
| Ethyl cinnamate | 2 |
| Isopropyl alcohol | 98 |
| Total | 100 |

The above components were mixed under stirring to give a homogeneous oil preparation.

EXAMPLE 2

| Emulsifiable Concentrate: | |
|---|---|
| | (parts by weight) |
| Cinnamyl acetate | 20 |
| Sorbitan monostearate | 10 |
| Xylene | 70 |

| Emulsifiable Concentrate: | |
|---|---|
| | (parts by weight) |
| Total | 100 |

The above components were mixed under stirring to give a homogeneous emulsion.

EXAMPLE 3

| Dust: | |
|---|---|
| | (parts by weight) |
| β-Phenoxyethyl alcohol | 10 |
| Silicic anhydride | 5 |
| Talc | 85 |
| Total | 100 |

The above components were intimately mixed to give a homogeneous dust.

EXAMPLE 4

| Dust: | (parts by weight) |
| --- | --- |
| Methyl phenylacetate | 40 |
| Soft polyvinyl chloride powder | 60 |
| Total | 100 |

The above components were stirred at room temperature over day and night to allow the polyvinyl chloride powder to absorb the methyl phenylacetate. Thus a dust was prepared.

EXAMPLE 5

| Detergent: | (parts by weight) |
| --- | --- |
| p-Cresyl butyrate | 10 |
| Polyoxyethylene nonylphenyl ether | 25 |
| water | 65 |
| Total | 100 |

The above components were intimately mixed to give a homogeneous detergent.

EXAMPLE 6

| Aerosol: | (parts by weight) |
| --- | --- |
| Ethyl phenylacetate | 10 |
| Dimethoxyethane | 40 |
| Liquefied petroleum gas | 50 |
| Total | 100 |

The ethyl phenylacetate and dimethoxyethane were mixed under stirring and then introduced into an aerosol container. After providing a valve, the liquefied petroleum gas was fed thereinto through the valve under a pressure to give an aerosol.

EXAMPLE 7

| Aerosol: | (parts by weight) |
| --- | --- |
| p-Cresyl butyrate | 5 |
| Methyl diphenyl ether | 5 |
| Xylene | 10 |
| Illuminating kerosene | 30 |
| Liquefied petroleum gas/dimethyl ether mixture (ratio by volume = 1:1) | 50 |
| Total | 100 |

The above components except the mixture of liquefied petroleum gas and dimethyl ether were mixed under stirring and then introduced into an aerosol container. After providing a valve, the mixture of liquefied petroleum gas and dimethyl ether was fed thereinto through the valve under a pressure to give an aerosol.

EXAMPLE 8

| Sheet material: | (parts by weight) |
| --- | --- |
| Methyl phenylacetate | 20 |
| Ethyl cellulose | 10 |

| -continued Sheet material: | (parts by weight) |
| --- | --- |
| Ethanol | 70 |
| Total | 100 |

The above components were mixed under stirring, and a polyethylene pulp non-woven fabric was impregnated therewith in such a manner as to give a ratio of methyl phenylacetate of 1 g/m². Thus a sheet material was obtained.

EXAMPLE 9

| Sheet material: | (parts by weight) |
| --- | --- |
| Ethyl cinnamate | 10 |
| Dibenzyl ether | 10 |
| Ethyl cellulose | 10 |
| Ethanol | 70 |
| Total | 100 |

The above components were mixed under stirring, and a polyethylene pulp non-woven fabric was impregnated therewith in such a manner as to give a total amount of ethyl cinnamate and dibenzyl ether of 1 g/m². Thus a sheet material was obtained.

The acaricidal composition of the present invention exerts an excellent effect of extermination house dust acari. Further, it is highly safe to human body and can be easily applied in house, which makes it extremely advantageous.

While the invention has been described in detail and with reference to specific embodiments thereof, it will be apparent to one skilled in the art that various changes and modifications can be made therein without departing from the spirit and scope thereof.

What is claimed is:

1. A method for exterminating house dust acari, which comprises applying to an area or space infested with accari an acaricidal composition consisting essentially of one or more compounds selected from the group consisting of methyl cinnamate, ethyl cinnamate, n-propyl cinnamate, isopropyl cinnamate, n-butyl cinnamate, isobutyl cinnamate isoamyl cinnamate, n-hexyl cinnamate, allyl cinnamate, cinnamyl acetate, cinnamyl propionate, cinnamyl n-butyrate, cinnamyl isobutyrate, p-cresyl acetate, p-cresyl butyrate, p-cresyl isobutyrate, p-methylbenzyl propionate, β-phenoxyethyl alcohol, phenoxyethyl acetate, phenoxyethyl propionate, phenoxyethyl n-butyrate, phenoxyethyl isobutyrate, methyl phenylacetate, ethyl phenylacetate, dibenzyl ether, heliotropin, methyl diphenyl ether and 2-methyl-1-(methylbicyclo[2.2.1]hept-5-en-2-yl)-1-penten-3-ol as an active ingredient to a portion where dust acari inhabit, wherein the composition is applied in a dose of approximately 80 mg or more per m² of the area to be treated or approximately 8 mg or more per m³ of the space to be treated.

2. A method as claimed in claim 1, wherein said house dust acari are Dermatophagoides.

3. A method as claimed in claim 1, wherein the composition is applied in a dose of approximately 80 mg or more per m² of the area to be treated.

4. A method as claimed in claim 1, wherein the composition is applied in a dose of approximately 8 mg or more per m³ of the space to be treated.

5. A method as claimed in claim 1, wherein said one or more compounds is present in an amount of from 2 to 50% by weight.

* * * * *